United States Patent [19]

Campbell

[11] 4,416,822

[45] Nov. 22, 1983

[54] 17β-DIFLUOROMETHYL STEROIDS

[75] Inventor: J. Allan Campbell, Kalamazoo, Mich.

[73] Assignee: The Upjohn Company, Kalamazoo, Mich.

[21] Appl. No.: 396,968

[22] Filed: Jul. 9, 1982

[51] Int. Cl.³ .............................................. C07J 1/00
[52] U.S. Cl. ........................... 260/397.4; 260/397.45; 260/397.3; 260/239.5; 260/239.55 C; 424/243
[58] Field of Search ........................ 260/397.4, 397.45

[56] References Cited

U.S. PATENT DOCUMENTS 3,211,723 10/1965 Kagan ............................ 260/239.55

OTHER PUBLICATIONS

D. G. Martin, et al., The Reactions of Sulfur Tetarfluoride with Steroids, J. Org. Chem. 27, 3164 (1962).
D. G. Martin, et al., The Synthesis of 6α-Difluoromethyl Steroids, J. Org. Chem. 27, 4086 (1962).
Fieser and Fieser Reagents for Organic Synthesis, Wiley Interscience, vol. 6, p. 183.
Fieser and Fieser Reagents for Organic Synthesis, Wiley Interscience, vol 8, p. 166.
G. A. Olah, et al., Synthetic Methods and reactions I. Selenium Tetrafluoride and its Pyridine Complex, Convenient Fluorinating Agents for Fluorination of Ketones, Aldehydes, Amides, Alcohols, Carboxylic Acids, and Anhydrides, J. Am. Chem. Soc. 96, 925 (1974).
G. A. Boswell J. Org. Chem. 31, 991 (1966).
Chem. Abst. 85, 124237g.

Primary Examiner—Elbert L. Roberts
Attorney, Agent, or Firm—Bruce Stein

[57] ABSTRACT

17β-Difluoromethyl steroids are disclosed which have progestational, antiprogestational activity and which are useful as and male and female contraceptive agents.

12 Claims, No Drawings

17β-DIFLUOROMETHYL STEROIDS

BACKGROUND OF THE INVENTION

The process of transforming a 17-keto steroid to the corresponding steroid with an aldehyde at $C_{17}$ by addition of a carbon atom is known to those skilled in the art. See, for example, C. Byon et al. in J. Org. Chem. 45, 4404 (1980) and references therein; Chem. Abst. 85, 124237g; and East German Pat. No. 117,673.

Aldehydes can be transformed to the corresponding difluoromethyl compound by reaction with selenium tetrafluoride, see Olah et al., J. Am. Chem. Soc. 96, 925 (1974), with sulfur tetrafluoride, see Martin and Kagan, J. Org. Chem. 27, 3164 (1962), or with diethylaminosulfur trifluoride, see Fieser and Fieser, Reagents for Organic Synthesis, Wiley Interscience, Vol. 6, p. 183 and Vol. 8, p. 166.

17,17-Difluoroandrost-4-en-3-one and 20,20-difluoroprogesterone are known, see Martin, supra. The 20,20-difluoromethylprogesterone of Martin was disclosed to possess central nervous system depressant activity which made the agents useful as sedatives and general anesthetics in mammals. U.S. Pat. No. 3,211,723 discloses that 20,20-difluoropregnane-11-one exhibits activity as an anti-fertility agent and can be used in controlling fertility in ovulating mammals and birds, for example, in animals such as swine, cattle, horses, sheep, dogs, cats and the like.

6α-Difluoromethyl corticoids are known, see Martin and Pike, J. Org. Chem. 27, 4086 (1962). 6,6-Difluoro-17α-acetoxyprogesterone is known, see G. A. Boswell, J. Org. Chem. 31, 991 (1966). However, Fried and Edwards in Organic Reactions in Steroid Chemistry, Van Nostrand, 1972, in Volume 1, devote Chapter 8 to Introduction of Fluorine Into The Steroid System. In 65 pages of discussion of fluorinated steroids, trifluoromethyl steroids were mentioned (p. 470) and the difluoromethylene steroids in the Martin et al. publications were discussed. Difluoromethyl steroids were not discussed.

SUMMARY OF THE INVENTION

Disclosed are 17β-difluoromethyl steroids (IV) as well as 9-unsaturated 17β-difluormethyl steroids (VIII), $\Delta^{9(11)}$-17β-difluoromethyl steroids (XI), 9,11-disubstituted 17β-difluoromethyl steroids (XII) which are useful as male and female contraceptive agents.

DETAILED DESCRIPTION OF THE INVENTION

Refer to Charts A–D.

The 17β-difluoromethyl steroids (IV, VIII and XI) are prepared from the corresponding steroidal 17-aldehydes (III, VII and X, respectively).

The steroidal 17-aldehydes (III, VII and X) are either well known to those skilled in the art or can be readily prepared from the corresponding $C_3$-protected 17-keto steroids (I, V, IX) by methods well known to those skilled in the art, see, for example, Byon et al., J. Org. Chem. 45, 4404 (1980). The 17-keto steroids (I) are protected as the ketal (IA) enamine (IB) or enol ether (IC); the 17-keto steroid (V) is protected as the enol ether; and the 17-keto steroid (IX) is protected as the ketal, enamine or enol ether as is well known to those skilled in the art. With the $C_3$-protected 17-keto steroid (I) and the $C_3$-protected $\Delta^{17(20)}$ steroid (II), it is realized when "⋮⋮⋮" is a double bond, the $R_6$ substituent is neither α nor β. The $C_3$ protected 17-keto steroid is reacted with methoxymethyltriphenylphosphonium chloride under basic conditions to produce the cis/trans isomeric mixture of the enol ether 20-methoxy-17(20)-unsaturated steroid (II and VI). The enol ether is then converted under acidic conditions to the corresponding steroidal 17-aldehyde.

The steroidal 17-aldehydes (III, VII or X) are reacted in a dry non-polar solvent such as halogenated hydrocarbons, toluene, benzene, cyclohexane, hexane, THF, and diethyl ether. The preferred solvent is methylene chloride. The fluorinating agent either in pure form or in an organic solvent is contacted with the steroidal 17-aldehyde. It is preferred that the fluorinating agent be diethylaminosulfur trifluoride and it should be added in an excess. The reaction is carried out in a temperature range of $-20°$ to $50°$, preferably, and most conveniently at $20°-25°$. The reaction progress is monitored by TLC and is usually complete in a few hours to a day. When the reaction is complete as monitored by TLC, water is added followed by base. Alternatively, an aqueous basic solution such as bicarbonate or carbonate can be added. A water immiscible organic solvent is used to extract out the steroid product. The organic phase is separated, dried and concentrated under reduced pressure to give a 17β-difluoromethyl steroid product. With regard to the 17β-difluoromethyl steroids (IV) of Chart A, the 17β-difluoromethyl steroid (IV) produced is the desired therapeutically active compound. It is purified by means well known to those skilled in the art, preferably by chromatography. For the 9-unsaturated-17β-difluoromethyl steroids (VIII) of Chart B, the product of the fluorination reaction is a 17β-difluoromethylestr-5(10)-en-3-one which, upon reaction with pyridinium bromide perbromides according to the procedure of Perelman et al., J. Am. Chem. Soc. 82, 2402 (1960), produces the desired therapeutically active 9-unsaturated-17β-difluoromethyl steroid (VIII). With regard to the 9,11-disubstituted-17β-difluoromethyl steroids (XII) of Chart C, the fluorination reaction produces a 17β-difluoromethylandrost-4,9(11-dien-3-one (XI), which is reacted with (1) HOBr, an epoxidating means such as potassium acetate in ethanol and treatment of the epoxide with HF; (2) $Cl_2$; or (3) BrF by means well known to those skilled in the art to produce the desired 9α-fluoro-11β-hydroxy-17β-difluoromethylandrost-4-en-3-one (XII), 9α,11β-dichloro-17β-difluoromethylandrost-4-en-3-one (XII) and 9α-bromo-11β-fluoro-17β-difluoromethylandrost-4-en-3-one (XII), respectively, which are the therapeutically active compounds.

The 17β-difluoromethyl steroids (IV, VIII, XI and XII) have progestational, antiprogestational and male and female antifertility activity and therefore are useful as male and female contraceptive agents in humans and other mammals.

The 17β-difluoromethyl steroids (IV, VIII, XI and XII) may be used either individually or in combination with each other for their contraceptive effect.

The 17β-difluoromethyl steroids (IV, VIII, XI and XII) which have either progestational or antiprogestational activity are useful as male and female contraceptive agents and are used to provide reversible contraception for male and female mammals post-puberty which are selected from the group consisting of man, male dog, tom, bull, stallion, ram, boar, male rat and male mouse and their female counterparts.

With regards to the human, there are many instances in which the female cannot take various types of chemical contraceptive agents and does not or cannot use various physical contraceptive devices such as IUD (IUCD) or diaphragm. In addition, many women do not wish to rely on non-prescription (over-the-counter) foams, gels and cream chemical contraceptive agents. Therefore, there are numerous instances in which it would be highly desirable to have a reliable reversible contraceptive agent for men. This is particularly true in view of the fact that the only reversible contraceptive agent for man is a mechanical device (prophylactic) which has the distinct disadvantage of low efficacy. In addition, there is the disadvantage of mechanical devices of having to interrupt intercourse to properly position the device.

The useful warm blooded animals can be divided into two groups—domesticated (dog, tom) and commercial (bull, stallion, ram and boar). The domesticated male animals usually cohabitate with the females. The commercial male animals are usually separated from the females because either it is desired that the particular males not fertilize the females so that artificial insemination may be used, or even if the particular males are well suited to fertilizing the females it may be desired that they do not do so at the present time. The use of the methods of the present invention permits one to allow both the domestic and commercial male and females to cohabitate without sterilization of either sex and without unwanted pregnancies and still retain the flexibility of fertilizing the female when desired either with a desired male or by artificial insemination.

With regards to the rodents, the rat and mouse, it is highly desirable of course to be able to eradicate or control the populations of these rodents with the methods of the present invention. These rodents can be controlled and/or eradicated by decreasing the fertility of these rodents by use of the methods of th present invention. This of course would not eliminate the rodents which are present, but only future rodents which these animals might conceive, thereby decreasing future populations of these undesirable animals.

The $17\beta$-difluoromethyl steroids (IV, VIII, XI and XII) which are useful as male contraceptive steroids are administered such that the male mammal receives about 0.01 to about 1.0 mg/kg/day. For a 70 kg male, the amount would be about 0.7 to about 70 mg/day.

The $17\beta$-difluoromethyl steroids (IV, VIII, XI and XII) useful as female contraceptive agents are administered such that the female mammal receives about 0.01 to about 1.0 mg/kg/day. For a 50 kg female, the amount would be about 0.5 to about 50 mg/day.

The exact dose of the $17\beta$-difluoromethyl steroids (IV, VIII, XI and XII) will depend on the particular compound, the weight, age, and physical condition of the particular patient to be treated.

It is necessary to pretreat the male mammals approximately 30–90 days in order to obtain the desired contraceptive effect. The length of time of pretreatment will depend on the particular $17\beta$-difluoromethyl steroid (VI, VIII, IX and XII) and the particular animal. The female mammals should be pretreated approximately 1 cycle depending on when in the cycle administration is begun.

The $17\beta$-difluoromethyl steroid (IV, VIII, IX, and XII) contraceptive agents administered by oral, parenteral, in sustained release form, intrauterine, intravaginal means in the appropriate dosage forms.

Oral dosage forms include both solid and liquid. The solid dosage forms include tablets (compressed, tablet triturates, enteric coated, sugar coated, film coated and multiple compressed), capsules (hard and soft gelatin), treats, bait, veterinary premix and animal feed. The liquid oral dosage forms include, for example, aqueous solutions (elixirs and syrups), emulsions, and suspensions. In the parenteral sustained release form, the active ingredient is slowly released over a prolonged period as is well known to those skilled in the art. These preparations are known as sustained release parenteral forms or depo forms.

One method of formulating parenteral depo compositions is to administer the drug dissolved in or suspended in oil. An oleoginous solution or suspension injected intramuscularly provides a depo which slowly releases the drug to tissue fluid and the blood. The oil may be modified by the inclusion of wax or some other water-repellant substance such as aluminum stearate which further reduces the release rate of the therapeutically active ingredient.

An alternative long acting parenteral composition is one where the relatively water-insoluble $17\beta$-difluoromethyl steroid (IV, VIII, XI or XII) is suspended in an aqueous medium. The aqueous medium can be modifed by the addition of certain hydrocolloids such as gelatin, carboxymethyl cellulose or polyvinylpyrrolidone. The contraceptive steroids of the present invention are quite water-insoluble and those which are crystalline lend themselves very well to this type of formulation.

Long acting parenteral steroidal compositions in oil are well known to those skilled in the art. For example, see testosterone cypionate USP (See Physicians Desk Reference, PDR, 31 edition, 1977, page 1625); nandrolone phenpropionate N.F. (PDR, ibid., page 1138); estradiol cypionate injection USP and testosterone enanthate USP (PDR, ibid., page 1512) which is advertised as having a duration of action of about 4 weeks.

Long acting aqueous parenteral compositions are also well known to those skilled in the art. See British Pat. Nos. 705,343 and 731,933. Various long acting aqueous parenteral steroidal preparations are well known to those skilled in the art. See British Pat. Nos. 731,933, Examples 1–4 and methylprednisolone acetate suspension N.F. (PDR, ibid., page 1623) and medroxyprogesterone acetate suspension (PDR, ibid., page 1625).

U.S. Pat. No. 4,038,389 discloses and claims aqueous parenteral compositions containing 200–600 mg/ml of medroxyprogesterone. The usual therapeutic dose of medroxyprogesterone is 2.5–10 mg, see PDR, ibid., page 1648, where the product is marked in oral tablet form at two dose levels, 2.5 and 10.0 mg. The very high dose of medroxyprogesterone disclosed in U.S. Pat. No. 4,038,389 is obviously because it is in long acting (depo) form intended to have a duration of action of many weeks. See The Journal of Reproductive Physiology 13, 113 (1974), where the composition claimed in U.S. Pat. No. 4,038,389 had a duration of action of at least 3 months in preventing pregnancy.

Recently (1977), five papers appeared in the journal Contraception, Vol. 15, at pages 627, 635, 649, 669 and 679, which show that testosterone can be administered parenterally in a form which will provide effective amounts of testosterone for a period of at least one month.

Therefore, the technology is known to those skilled in the art to formulate the $17\beta$-difluoromethyl contraceptive steroids of the present invention into depo or long acting parenteral preparations. The depo parenteral preparations should release the male contraceptive steroid at the rate of about 0.01 to about 1.0 mg/kg/day.

An alternative pharmaceutical composition to deliver the 17β-difluoromethyl contraceptive steroids to the desired animal at a controlled rate over a long period of time is the implant. The technology for formulating the proper implants is well known to those skilled in the art. The J. of Animal Science 35, 251 (1972), in an article by M. L. Ogilvie, describes a polyurethane implant containing melengesterol acetate which was used in heifers for over four months. John B. Herrick in Animal Nutrition and Health, April 1977, at page 23, describes a number of growth promotants for beef cattle. Many of these growth promotants are steroids, including testosterone, and are administered by implants. L. L. Ewing et al., in Contraception 13, 583 (1976), describes a method of decreasing sperm counts in male rhesus monkeys by administering testosterone via subdermal dimethylpolysiloxane implants. The implants were left in for 70 days, and the results demonstrate the satisfactory nature of this method. W. E. Johansson et al., in Contraception 13, 287 (1976), describes using dimethylpolysiloxane implants containing a steroid in women for over four months. Further, U.S. Pat. No. 3,896,819 discloses a drug delivery device for administering a drug at a controlled rate for a prolonged period of time. The drug delivery device can be used as an implant, see column 6, starting at line 55. This implant is useful with steroids such as methyltestosterone, see column 19, starting at line 24. The implant should release the 17β-difluoromethyl contraceptive steroids of the present invention at the rate of about 0.01 to about 1.0 mg/kg/day.

The pharmaceutically therapeutically active 17β-difluoromethyl contraceptive steroids of the present invention are administered orally or parenterally in unit-dosage forms or multiple-dosage forms. Unit-dose forms refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampuls and syringes (parenteral) and individually packaged tablet or capsule (oral-solid). Unit-dose forms may be administered in fractions or multiples thereof. A multiple-dose form is a plurality of identical unit-dosage forms packaged in a single container to be administered in segregated unit-dose form. Examples of multiple-dose forms include vials (parenteral) and bottles of tablets of capsules (oral-solid). Hence, multiple dose forms is a multiple of unit-doses which are not segregated in packaging. The specifications for the unit-dosage form and the multiple-dosage form are dictated by and directly dependent on (a) the unique characteristics of the particular 17β-difluoromethyl steroid (IV, VIII, XI or XII) and the particular therapeutic effect to be achieved and (b) the limitations inherent in the art of compounding such a therapeutically active compound for reversible contraception.

The individual oral solid pharmaceutical dosage forms, tablets and capsules, are packaged individually (unit dose) or in quantity (multiple dose containers), for examples bottles of 50, 100, 500, 1,000 or 5,000. The amount of the 17β-difluoromethyl steroid (IV, VIII, IX and XII) per dosage unit (tablet or capsule) is adjusted so that the tablet or capsule, a fraction or multiple thereof, provides the patient with an effective amount. It is preferred that each tablet or capsule contain 1-250 mg of the 17β-difluoromethyl steroid (IV, VIII, IX and XII). The exact dosage depends on the particular compound, the age, weight, physical condition and particular patient or animal, as is known to those skilled in the art. Tablets and capsules are given in sufficient number and frequency to obtain the desired contraceptive effect.

U.S. Pat. No. 4,252,798 describes various dosage forms useful for a male contraceptive agent. While that patent describes dosage forms useful for a male contraceptive agent, those forms are equally applicable to the female contraceptive steroids of the present invention. U.S. Pat. No. 4,252,798 has a thorough discussion of sustained release tablets and capsules, tablet formulations used to treat dogs, cats and rabbits, treats, bait, liquid dosage forms, veterinary premixes, and animal feed compositions.

Following cessation of administration of the 17β-difluoromethyl steroids (IV, VIII, IX or XII), or at the end of the metering out of the parenteral sustained release formulation, contraception will be maintained only for a very short period, and gradually, the animal's ability to fertilize or be fertilized returns to normal.

DEFINITIONS

The definitions and explanations below are for the terms as used throughout the entire patent application including both the specification and claims.

All temperatures are in degrees Centigrade.

TLC refers to thin-layer chromatography.

THF refers to tetrahydrofuran.

SSB refers to an isometric mixture of hexanes.

Saline refers to an aqueous saturated sodium chloride solution.

IR refers to infrared spectroscopy.

UV refers to ultraviolet spectroscopy.

NMR refers to nuclear (proton) magnetic resonance spectroscopy, chemical shifts are reported in ppm ($\delta$) downfield from TMS.

MS refers to mass spectrometry expressed as m/e or mass/change unit.

When solvent pairs are used, the ratio of solvents used are volume/volume (v/v).

$R_3$ refers to alkyl of 1 thru 3 carbon atoms.

$R_6$ is a hydrogen atom or methyl group with the proviso that $R_6$ is a hydrogen atom when $R_7$ is a methyl group.

$R_7$ is a hydrogen atom or methyl group with the proviso that $R_7$ is a hydrogen atom when $R_6$ is a methyl group.

$R_9$ is a hydrogen, fluorine, chlorine or bromine atom.

$R_{10}$ is a hydrogen atom or methyl group.

$R_{11}$ is an oxygen, fluorine or chlorine atom or hydroxyl group.

Formulas (II) and (VI) do not disclose the stereochemistry at $C_{17}$. These formulas are meant to, and do, include both the cis and trans isomers.

Protecting group refers to ketal, enamine and enol ethers for the $\Delta^4$-3-keto starting materials (I) and (IX) of Charts A and C, respectively. Protecting group refers to enol ethers for the $\Delta^{2,5(10)}$-diene (V) starting material of Chart B.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants as well as reaction conditions and techniques.

Preparation 1

Cis and trans-17(methoxymethylene)estr-4-en-3-one 3-ethylene ketal (II) and cis and trans-17(methoxymethylene)estr-5(10)-en-3-one 3-ethylene ketal (II)

Potassium t-butoxide (1.6 N, 32 ml) in THF was added to dry toluene (200 ml). The mixture was concentrated under reduced pressure at slightly above 20°–25° until all the THF had been removed and a volume of about 150 ml had been reached. The concentrate was cooled in an ice bath and methoxymethyltriphenylphosphonium chloride was added in small portions under a nitrogen atmosphere. A solution previously dried by azeotropic distillation containing estr-5-ene-3,17-dione 3-ethylene ketal (I, 4 g), also known as 19-norandrostenedione 3-ketal in toluene (30 ml) was added to the previous mixture. The mixture was stirred at 20°–25° for 20 hours. The reaction mixture was then diluted with SSB (200 ml) and filtered through silica gel (100 g). The silica gel bed was washed with ethyl acetate/SSB (10/90). The filtrate and washings were combined and concentrated to an oil, identified as the title compounds.

Preparation 2

17β-Formylestr-4-en-3-one (III)

The crude product (II, Preparation 1) was dissolved in diethyl ether (200 ml) and perchloric acid (70%, 5 ml) was added. After about two hours, the reaction mixture was diluted with a little methylene chloride and washed with water bicarbonate dried over magnesium sulfate and concentrated to an oil. The oil was column chromatographed over silica gel (150 g), the column was eluted using gradient elution between 5 l of 5% ethyl acetate/SSB and 5 l of 30% ethyl acetate/SSB. The appropriate fractions were pooled and concentrated to give the title compound which was recrystallized from ether/methylene chloride. NMR (CDCl$_3$) 0.82, 5.80, and 9.76 δ.

Earlier fractions contained 20-monoethylene ketal (identified by its NMR), which was converted to the parent aldehyde by reaction with formic acid (98%) for 1.5 hrs. The aldehyde (III) was combined with the mother liquor from the previous crystallization and recrystallized from acetone to give additional title compound.

Preparation 3

Estra-3,5-dien-17-one 3-pyrrolidine enamine (I)

To 19-norandrost-4-en-3,17-dione (4.5 g) in boiling methanol (15 ml) was added pyrrolidine (2.25 ml). The enamine precipitated out immediately. The mixture was chilled and then filtered. The solids were washed with cold methanol and dried to yield the title compound.

Preparation 4

17β-Formylestra-4-en-3-one (III)

To estra-3,5-dien-17-one 3-pyrrolidine enamine (I, Preparation 3) in toluene (150 ml) was added potassium t-butoxide (1.6 N) in THF (28.5 ml) and methoxymethyltriphenylphosphonium chloride (15 g). Estra-3,5-dien-17-one 3-pyrrolidine enamine (I, Preparation 3) is added and after stirring for 24 hours, aqueous sodium bicarbonate was added and the toluene layer was separated and washed with water. The enamine product is extracted out of the toluene phase with cold 3 N hydrochloric acid (60 ml). The acid extract was concentrated slightly on the rotary evaporator to remove the trace of toluene. The solution was kept for 45 minutes and neutralized by dropwise addition of sodium hydroxide (2 N) to hydrolyze the enamine. As the enamine hydrolyzed, the keto-aldehyde product precipitated out. The precipitate was collected on a filter, washed well with water, and dissolved in methylene chloride, dried over magnesium sulfate and chromatographed through silica gel. The appropriate fractions were pooled and filtered through a short column of silica gel. The mixture was concentrated under reduced pressure to yield a solid which was recrystallized from acetone. NMR (CDCl$_3$) 0.82, 5.83, 9.78 δ.

Preparation 5

Cis- and Trans-17-(methoxymethylene)androst-4-en-3-one 3-pyrrolidine enamine (II)

Androst-4-ene-3,17-dione (10 g) in methanol (100 ml) was heated to boiling and pyrrolidine (7 ml) was added. The enamine (I) precipitates out almost immediately. After chilling the mixture, the enamine was filtered off and washed with cold methanol and dried under reduced pressure. The enamine and methoxymethyltriphenylphosphonium chloride (30 g) were stirred with toluene (700 ml), degassed under reduced pressure, releasing the vacuum with nitrogen. Solid potassium tertiary butoxide (10 g) was added to the stirred mixture. After stirring at 20°–25° for 20 hours, ice and water are added and the toluene phase separated and washed with water. The toluene phase was concentrated to dryness under reduced pressure. The solid was slurried with methanol (500 ml), purged with nitrogen, and sodium hydroxide (2 N, 25 ml) were added. The mixture was heated to boiling for 15 minutes to hydrolyze the enamine. The mixture was concentrated under reduced pressure to a volume of about 200 ml. Water was added and the product extracted with SSB containing a small amount of diethyl ether. The SSB extract was washed with methanol/water:60/40 and then with diluted hyrochloric acid and water. The SSB phase was dried and concentrated under reduced pressure to a solid. The solid was chromatographed through a silica gel column, eluting progressively with methylene chloride, 5% ethyl acetate/methylene chloride and 10% ethyl acetate/methylene chloride. The appropriate fractions are pooled and concentrated under reduced pressure. The product was recrystallized from acetone/SSB to give the title compund: NMR (CDCl$_3$) 0.84, 0.91, 1.91, 3.45, 3.54 and 5.70 δ.

Preparation 6

17β-Formylandrost-4-en-3-one (III)

Cis- and trans-(17-methoxymethylene)androst-4-en-3-one 3-pyrrolidine enamine (II, Preparation 5, 3.5 g) in diethyl ether (150 ml) was stirred and perchloric acid (70%, 3.5 ml) was added. After 15 minutes, the reaction was washed with water and bicarbonate. The ether layer was separated, dried and concentrated under reduced pressure to dryness. The residue was purified by trituration with diethyl ether to give the title compound. NMR (CDCl$_3$) 0.80, 1.19, 5.73 and 9.78 δ.

Preparation 7

17β-Formyl-7α-Methylestr-4-en-3-one (III)

Following the procedure of Preparations 5 and 6 and making noncritical variations but starting with 7α-methylestr-4-en-3,17-dione, the title compound was obtained. m.p. 207°–230°; UV (ethyl alcohol) λ$_{max}$ 241 nm ε=17,500; IR (mull) 2720, 1720, 1665, and 1620 cm$^{-1}$; MS (m/e) 300, 282, 272, and 258; NMR (CDCl$_3$) 0.78, 6.82, and 5.84 δ.

Preparation 8

Cis- and trans-3-hydroxy-17(methoxymethylene)estr-2,5(10)-diene 3-methyl ether (VI)

A slurry of methoxymethyltriphenylphosphonium chloride (15 g) in toluene (150 ml) was deoxygenated by evacuating and releasing the vacuum with nitrogen. The mixture was cooled in an ice bath and solid potassium tert-butoxide (5.1 g) was added portionwise. After about 15 minutes, 3-hydroxyestra-2,5(10)-dien-17-one 3-methyl ether (V, 5 g) in toluene (50 ml) was added. The mixture was stirred at 20°–25° for 48 hours. Ice was added and the toluene phase separated. The toluene phase was washed three times with water, dried and concentrated to an oil which was taken up in SSB. The mixture was extracted with methanol/water:60/40. The organic mixture was chromatographed through silica gel using toluene as the eluant. The appropriate fractions were pooled and concentrated to give the title compound. NMR (CDCl$_3$) 0.81, 0.83, 3.45, 3.54, 4.63, 5.66 and 5.69 δ.

Preparation 9

17β-Formylestr-5(10)-en-3-one (VII)

Silica gel (20 g) was deoxygenated by placing it under reduced pressure and releasing the pressure with nitrogen. The silica gel was stirred with methylene chloride (58 ml) and aqueous oxalic acid (5%, 2.8 ml) was added. After the aqueous phase was absorbed, cis- and trans-3-hydroxy-17-(methoxymethylene)estr-2,5(10)diene 3-methyl ether (VI, Preparation 8, 2 g) in methylene chloride (10 ml) was added. After one-half hour, TLC showed the reaction was not complete. Additional oxalic acid (10%, 1.4 ml) was added. After stirring for 22 hours, TLC showed the reaction to be complete. The acid was neutralized by the addition of solid sodium bicarbonate (390 mg). After the mixture was stirred for an additional 15 minutes, the mixture was filtered and the bed washed with a little diethyl ether. The material was chromatographed through silica gel, the appropriate fractions were pooled and concentrated to give the title compound. NMR (CDCl$_3$) 0.78 and 9.78 δ; MS (m/e) 286, 271, 257, 243 and 227.

EXAMPLE 1

17β-Difluoromethylestr-4-en-3-one (IV)

To a solution of 17β-formylestr-4-en-3-one (III, Preparation 2, 1.5 g) in methylene chloride (20 ml) was boiled to dry the system and then cooled under nitrogen with an ice bath. Diethylaminosulfurtrifluoride (0.6 ml) was added dropwise with a syringe. The mixture was kept at 20°–25° for several hours and then stirred at 5° overnight. A saturated aqueous sodium bicarbonate solution and diethyl ether were then added. The ether phase was separated, washed with water, dried over magnesium sulfate and chromatographed through silica gel using ethyl acetate/hexane; 30/70 as the eluant. The appropriate fractions were pooled and concentrated to a solid which was recrystallized from acetone/SSB to give the title compound. m.p. 102°–103°; UV (ethyl alcohol) λ$_{max}$ 239 nm, ε=17,250; IR (mull) 280, 266 and 110; MS (m/e) 308, and 293; NMR (CDCl$_3$) 0.84, 5.67, and 5.80 δ.

Anal. Calcd. for C$_{19}$H$_{26}$F$_2$O: C, 73.99; H, 8.50; F, 12.32. Found: C, 74.21; H, 8.51; F, 12.74.

EXAMPLE 2

17β-Difluoromethyl-7α-methylestr-4-en-3-one (IV)

Following the general procedure of Example 1 and making noncritical variations but starting with 17β-formyl-7α-estr-4-en-3-one (III, Preparation 7, 2.0 g), the title compound was obtained. m.p. 131°–135°; UV (ethyl alcohol) λ$_{max}$ 241 nm, ε=17,450; IR (mull) 1670, and 1613 cm$^{-1}$; MS (m/e)=322, 307, 294, and 280; NMR (CDCl$_3$) 0.88, 0.83, 5.85, and 5.72 δ.

EXAMPLE 3

17β-Difluoromethylandrost-4-en-3-one (IV)

Following the general procedure of Example 1 and making noncritical variations but starting with androst-4-en-3-on-17-al (III, Preparation 6, 1.9 g), the title compound was obtained. m.p. 137°–140°; UV (ethyl alcohol) λ$_{max}$ 241 nm, ε=17,000; IR (mull) 1668, 1610 cm$^{-1}$; MS (m/e)=322, 240, 265 and 237; NMR (CDCl$_3$) 0.81, 1.19, 5.74, and 5.2 δ.

EXAMPLE 4

17β-Difluoromethylestr-4,9-dien-3-one (VIII)

Following the general procedure of Example 1 and making noncritical variations but starting with 17β-formylestr-5(10)-en-3-one (VII, Preparation 9), 17β-difluoromethylestra-4,9-dien-3-one is produced.

The 17β-difluoromethylestr-5(10)-en-3-one is dissolved in pyridine under nitrogen with stirring. Pyridinium bromide perbromide is added over a 5-minute period. The reaction is stirred at 20°–25° under nitrogen for about 2.5 hr. Water is then added and the product extracted with diethyl ether. The diethyl ether extract is washed with water, dilute hydrochloric acid, water, dilute bicarbonate, water, and chromatographed over a silica gel column. The column is eluted with a gradient between 10% ethyl acetate-SSB and 60% ethyl acetate-SSB. The appropriate fractions are pooled and concentrated. The concentrate is rechromatographed and recrystallized from acetone to give the title compound.

EXAMPLE 5

17β-Difluoromethylandrost-4,9(11)-dien-3-one (XI)

Following the general procedure of Example 1 and making noncritical variations but starting with 17β-formylandrosta-4,9(11)-dien-3-one (X) the title compound is obtained.

EXAMPLE 6

9α-Chloro-11β-fluoro-17β-difluoromethylandrost-4-en-3-one (XII)

To a solution of 2.9 ml of liquid hydrogen fluoride and 2.0 ml of THF previously cooled to −78° under nitrogen is added a solution of 17b-difluoroandrosta-4,9(11)-dien-3-one (XI, Example 5, 1.5 g) with 10–15 ml of methylene chloride. After termal equilibrium is obtained, solid N-chlorosuccinimide (0.8 g) is added and the mixture stirred at −78° for approximately 3 hrs. The mixture is warmed to −20° over a 25 min period and then warmed to 0° over the next 30 min and then poured slowly into an ice-cooled solution of potassium carbonate (15 g) and water (50 ml). The phases are separated and the aqueous phase is washed twice with methylene chloride. The organic phases are combined and washed with a solution of sodium sulfite (2.5 g in 30 ml), dried over sodium sulfate and concentrated under reduced pressure to give a solid which is purified by column chromatography to give the title compound.

EXAMPLE 7

9α-Bromo-11β-fluoro-17β-difluoromethylandrost-4-en-3-one (XII)

Following the general procedure of Example 8 and making noncritical variations but using 1,3-dibromo-5,5-dimethylhydantoin (dibromotin) in place of N-chlorosuccinamide the title compound is obtained.

EXAMPLE 8

A 60 kg, 26-year-old female, who is the mother of two children, is given one 40-mg tablet daily of a 17β-difluoromethyl steroid (IV, VIII, XI or XII). After 60 days it is found that following sexual intercourse she is not fertilized by the father of her two previous children at the most fertile time of her cycle.

EXAMPLE 9

A 70 kg, 20-year-old man is treated daily with 1 teaspoonful (55 mg) of a suspension of a 17β-difluoromethyl steroid (IV, VIII, XI or XII). After 60 days, it is found that following sexual intercourse he does not fertilize a fertile female (who has previously delivered a child) a the most fertile time of her cycle. Upon further administration, the male remains infertile.

EXAMPLE 10

A 6 kg tom, who has previously sired offspring, was given a treat daily containing 10 mg of a 17β-difluoromethyl steroid (IV, VIII, XI or XII). After 60 days it is found that following sexual intercourse the animal does not fertilize an ovulating female (who has previously delivered young) at the time of her estrus. Upon continuous daily administration of the treat to the tom, the animal remains infertile. Eighty days following cessation of administration of the treat, the tom, upon sexual intercourse, fertilizes the same ovulating female at the time of her estrus.

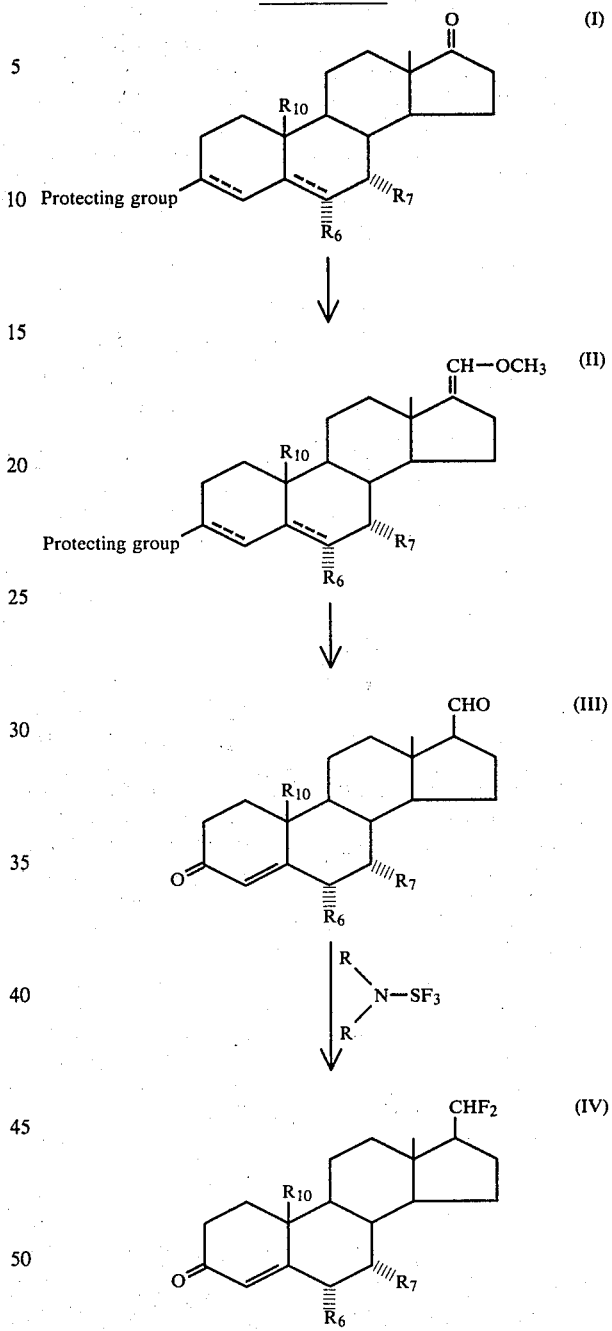

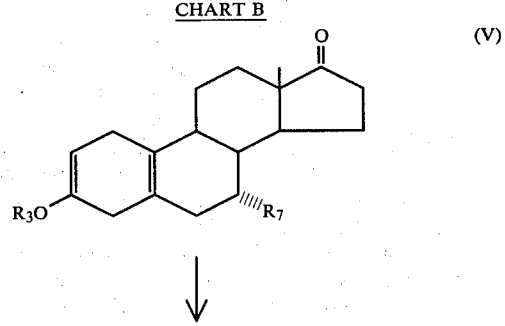

4,416,822
-continued
CHART B
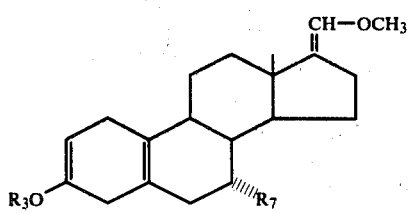 (VI)
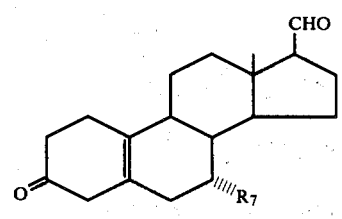 (VII)
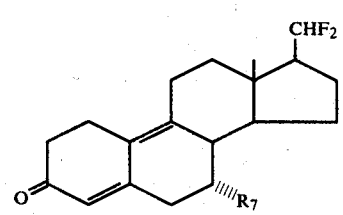 (VIII)
CHART C
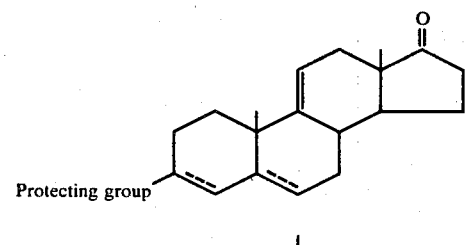 (IX)
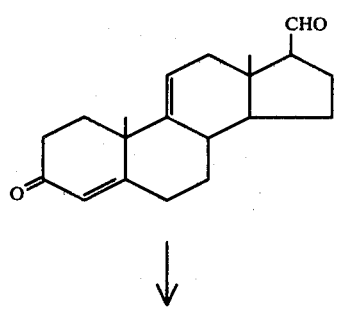 (X)
-continued
CHART C
 (XI)
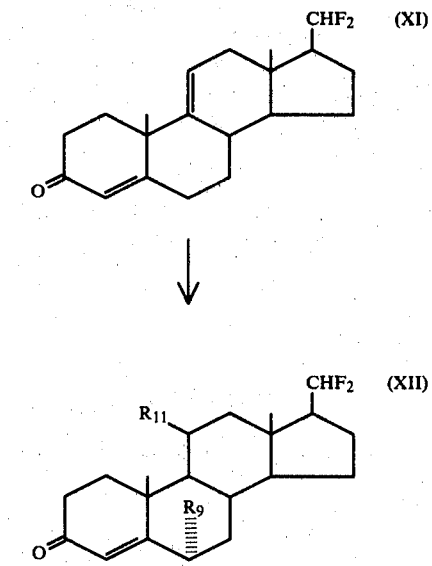 (XII)
CHART D
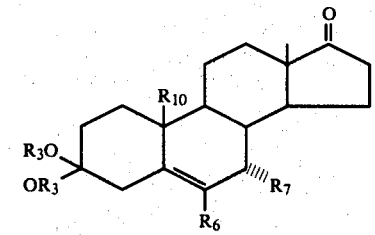 (IA)
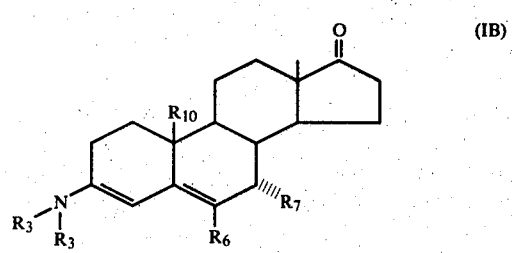 (IB)
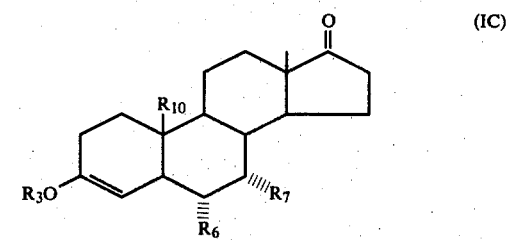 (IC)
I claim:
1. A 17β-difluoromethyl steroid of the formula

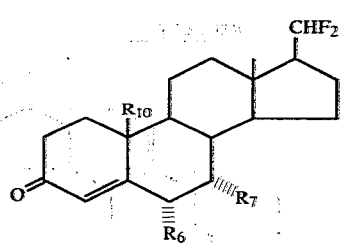

(IV)

where $R_6$ is a hydrogen atom or methyl group with a proviso that $R_6$ is a hydrogen atom when $R_7$ is a methyl group; where $R_7$ is a hydrogen atom or methyl group with a proviso that $R_7$ is a hydrogen atom when $R_6$ is a methyl group; and $R_{10}$ is a hydrogen atom or methyl group.

2. A 17β-difluoromethyl steroid according to claim 1 where $R_6$ is a hydrogen atom.

3. A 17β-difluoromethyl steroid according to claim 1 where $R_7$ is a hydrogen atom.

4. A 17β-difluoromethyl steroid according to claim 1 which is 17β-difluoromethylestr-4-en-3-one.

5. A 17β-difluoromethyl steroid according to claim 1 which is 17β-difluoromethyl-7α-methylestr-4-en-3-one.

6. A 17β-difluoromethyl steroid according to claim 1 which is 17β-difluoromethylandrost-4-en-3-one.

7. A 9-unsaturated steroid of the formula

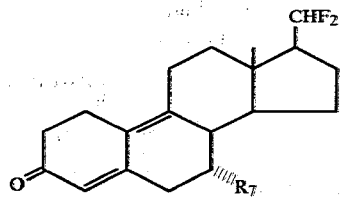

(VIII)

where $R_7$ is defined in claim 1.

8. A 9-unsaturated steroid according to claim 7 which is 17β-difluoromethylester-4,9-dien-3-one.

9. A $\Delta^{9(11)}$-steroid of the formula

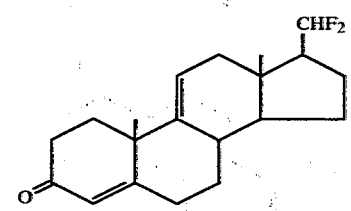

(XI)

10. A 9,11-disubstituted steroid of the formula

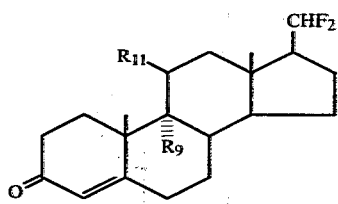

(XII)

where $R_9$ is a hydrogen, fluorine, chlorine or bromine atom; and $R_{11}$ is an oxygen, fluorine or chlorine atom or hydroxyl group.

11. A 9,11-disubstituted steroid according to claim 10 which is 9α-chloro-11β-fluoro-17β-difluoromethyland-rost-4-en-3-one.

12. A 9,11-disubstituted steroid according to claim 10 which is 9α-bromo-11β-fluoro-17β-difluoromethyland-rost-4-en-3-one.

* * * * *